United States Patent
Niemela et al.

(10) Patent No.: US 11,537,912 B2
(45) Date of Patent: Dec. 27, 2022

(54) GENERATING AND APPLYING ROBUST DOSE PREDICTION MODELS

(71) Applicant: Varian Medical Systems International AG., Cham (CH)

(72) Inventors: Perttu Niemela, Espoo (FI); Jari Lindberg, Helsinki (FI); Tuomas Jyske, Vantaa (FI); Maria Cordero Marcos, Espoo (FI); Esa Kuusela, Espoo (FI)

(73) Assignee: Varian Medical Systems International AG, Cham (CH)

( * ) Notice: Subject to any disclaimer, the term of this patent is extended or adjusted under 35 U.S.C. 154(b) by 492 days.

(21) Appl. No.: 16/795,143

(22) Filed: Feb. 19, 2020

(65) Prior Publication Data
US 2021/0256399 A1 Aug. 19, 2021

(51) Int. Cl.
| | | |
|---|---|---|
| *A61N 5/10* | (2006.01) | |
| *G06N 5/04* | (2006.01) | |
| *G16H 20/40* | (2018.01) | |
| *G06N 20/00* | (2019.01) | |

(52) U.S. Cl.
CPC ............. *G06N 5/04* (2013.01); *A61N 5/1031* (2013.01); *G06N 20/00* (2019.01); *G16H 20/40* (2018.01); *A61N 2005/1041* (2013.01)

(58) Field of Classification Search
None
See application file for complete search history.

(56) References Cited

U.S. PATENT DOCUMENTS

| | | | |
|---|---|---|---|
| 2009/0234626 A1 | 9/2009 | Yu et al. | |
| 2013/0150646 A1* | 6/2013 | Scholz | A61N 5/1031 600/1 |
| 2015/0095043 A1 | 4/2015 | Cordero Marcos et al. | |
| 2018/0117357 A1* | 5/2018 | Fredriksson | A61N 5/103 |
| 2021/0228907 A1* | 7/2021 | Olcott | A61N 5/1038 |

FOREIGN PATENT DOCUMENTS

| | | |
|---|---|---|
| EP | 3395405 | 10/2018 |
| WO | 2015042727 | 4/2015 |
| WO | 2019016305 | 1/2019 |

\* cited by examiner

*Primary Examiner* — Hoon K Song (57) ABSTRACT

Nominal values of parameters, and perturbations of the nominal values, that are associated with previously defined radiation treatment plans are accessed. For each treatment field of the treatment plans, a field-specific planning target volume (fsPTV) is determined based on those perturbations. At least one clinical target volume (CTV) and at least one organ-at-risk (OAR) volume are also delineated. Each OAR includes at least one sub-volume that is delineated based on spatial relationships between each OAR and the CTV and the fsPTV for each treatment field. Dose distributions for the sub-volumes are determined based on the nominal values and the perturbations. One or more dose prediction models are generated for each sub-volume. The dose prediction model(s) are trained using the dose distributions.

20 Claims, 6 Drawing Sheets

GENERATING AND APPLYING ROBUST DOSE PREDICTION MODELS

BACKGROUND

The use of radiation therapy to treat cancer is well known. Typically, radiation therapy involves directing a beam of high energy proton, photon, ion, or electron radiation ("therapeutic radiation") into a target, or target volume (e.g., a volume that includes a tumor or lesion).

Before a patient is treated with radiation, a treatment plan specific to that patient is developed. The plan defines various aspects of the therapy using simulations and optimizations based on past experiences. In general, the purpose of the treatment plan is to deliver sufficient radiation to the unhealthy tissue while minimizing exposure of surrounding healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is optimized (best suited) to achieve the desired outcome.

A critical component of treatment planning is predicting the dosage and dose distribution of the radiation to be applied to the patient. In knowledge-based dose prediction, information from previously planned radiation treatments can be used to gain knowledge of what is an achievable dose distribution in a new case without performing the actual planning. One approach to knowledge-based dose prediction is to use a set of treatment plans to create a model that can then be used to predict the dose for a new case. The prediction can be transformed into optimization objectives that, when used in combination with an optimization algorithm, produce a complete treatment plan.

SUMMARY

It is desirable for the dose prediction models to be "robust," so that they account for perturbations that can occur during treatment. For example, a patient's position may change during treatment, and preferably the dose prediction model can account for patient movement when the model is used to optimize the objectives of a radiation or radiotherapy treatment plan prior to treating the patient.

Embodiments according to the present invention provide an improved method of radiation treatment planning. More specifically, embodiments according to the invention pertain to the generation of robust dose prediction models, and to the application of those models to develop and optimize radiation treatment plans.

In embodiments, nominal values of parameters, and perturbations of the nominal values, that are associated with previously defined radiation treatment plans are accessed. For each treatment field of those treatment plans, a field-specific planning target volume (fsPTV) is determined based on the perturbations. At least one clinical target volume (CTV) and at least one organ-at-risk (OAR) volume are also delineated. Each OAR includes at least one sub-volume that is delineated based on spatial relationships between each OAR and the CTV and the fsPTV for each treatment field. Dose distributions for the sub-volumes are determined based on the nominal values and based on the perturbations. For example, if there are N perturbations, then N+1 dose distributions are determined: a dose distribution based on the nominal values, and a dose distribution based on each of the perturbations.

In embodiments, multiple robust dose prediction models are generated for each sub-volume. For example, if there are N perturbations, then N+1 dose prediction models are generated for each sub-volume: a dose prediction model that is trained using the dose distribution based on the nominal values, and a dose prediction model that is trained using each dose distribution based on each of the perturbations.

In other embodiments, only one robust dose prediction model is generated for each sub-volume. However, that model is trained using all of the dose distributions. For example, if there are N perturbations, then the dose prediction model is trained using the N+1 dose distributions described above.

Thus, in embodiments according to the present invention, robust dose prediction models are generated that are trained on and as such account for potential perturbations in plan parameters during treatment.

In embodiments in which multiple robust dose prediction models are generated per sub-volume, when the models are applied to a radiation treatment plan, the perturbations are inserted as parameters into the models to develop the optimization objectives. More specifically, the models are used to predict dose-volume histograms (DVHs) for the plan. If there are N perturbations and therefore N+1 models, then a set of N+1 DVHs per sub-volume are determined for the plan. The dose prediction models can then be used to generate the optimization objectives based on the DVHs.

In embodiments in which only a single robust dose prediction model is generated per-sub-volume, that model is used to predict a nominal DVH per sub-volume. The dose prediction model can then be used to generate the optimization objectives based on the nominal DVH.

Embodiments according to the invention improve radiation treatment planning, and hence the treatment itself, by increasing the robustness of the dose prediction models, which are in turn used to develop and optimize radiation treatment plans for the benefit of the patients being treated. Robust models can be utilized to deliver sufficient doses to the CTV in perturbed treatment scenarios while ensuring that OARs do not receive too much dose in any perturbed scenario. Robust models are particularly important for proton beam treatments but are important as well for other modalities.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "generating," "applying," "representing," "indicating," "storing," "using," "adjusting," "including," "computing," "calculating," "associating," or the like, refer to actions and processes (e.g., the flowcharts of FIGS. 1A, 2, 4, and 5) of a computer system or similar electronic computing device or processor (e.g., the computer system 600 of FIG. 6). The computer system or similar electronic computing device manipulates and transforms data represented as physical (electronic) quantities within the computer system memories, registers or other such information storage, transmission or display devices. Terms such as "dose," "dose rate," or some other parameter or attribute generally refer to a dose value, dose rate value, attribute value, or parameter value, respectively; the use of such terms will be clear from the context of the surrounding discussion.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

Portions of the detailed description that follows are presented and discussed in terms of methods. Although steps and sequencing thereof are disclosed in figures herein (e.g., FIGS. 1A, 2, 4, and 5) describing the operations of those methods, such steps and sequencing are examples only. Embodiments are well-suited to performing various other steps or variations of the steps recited in the flowcharts of the figures herein, and in a sequence other than that depicted and described herein.

FIGS. 1A, 2, 4, and 5 are flowcharts 100, 200, 400, and 500, respectively, of examples of computer-implemented operations for generating dose prediction models or applying such models to radiation treatment plans in embodiments according to the present invention. The flowcharts 100, 200, 400, and 500 can be implemented as computer-executable instructions (e.g., the models 650 and 651 of FIG. 6) residing on some form of computer-readable storage medium (e.g., in memory of the computer system 600 of FIG. 6).

Figure 1A:
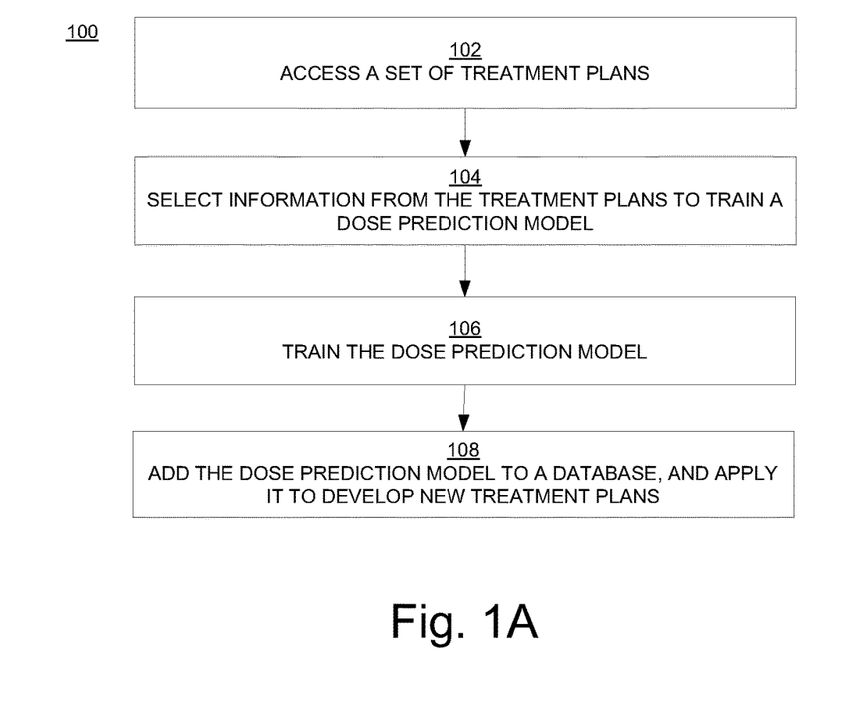
FIG. 1A is a flowchart of a computer-implemented method of generating and applying a dose prediction model in embodiments according to the present invention.

FIG. 1A is a flowchart 100 that provides an overview of a computer-implemented method of generating and applying a dose prediction model in embodiments according to the present invention. FIG. 1A is discussed with reference also to FIG. 1B, which is a block diagram illustrating elements in the process of FIG. 1A.

Figure 1B:
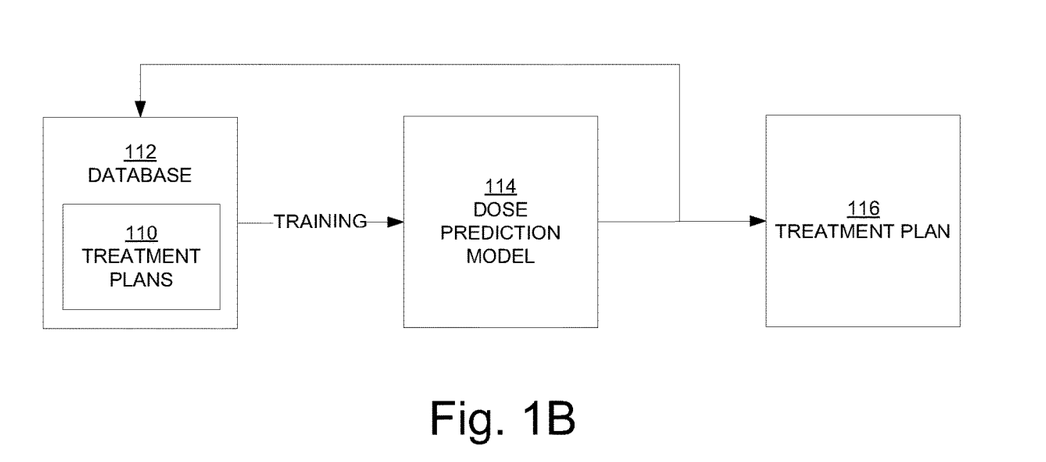
FIG. 1B is a block diagram illustrating elements in a method of generating and applying a dose prediction model in embodiments according to the present invention.

In block 102, a set of previously defined treatment plans 110 are accessed from a treatment plan database (e.g., a knowledge-based database 112).

In block 104, information in those treatment plans, such as information for each organ-at-risk (OAR) and dose-volume histograms (DVHs), is selected for use in training a new dose prediction model.

In block 106, a new dose prediction model 114 is trained. In embodiments, the training process includes identification of acceptable clinical goals, including acceptable trade-offs between target dose coverage versus doses to organs-at-risk (OARs). The training process can also include calculating DVHs using the model being trained, which can be compared to the DVHs in the treatment plan training set.

In block 108, once the prediction model is trained, it can be added to the database 112 or to another database, and it can also be used to predict DVHs and doses for a treatment plan 116 being developed for radiation treatment of a patient. The dose prediction model can be used for developing treatment plans for, but not limited to, intensity-modulated radiotherapy (IMRT) and volumetric modulated arc therapy (VMAT).

Figure 2:
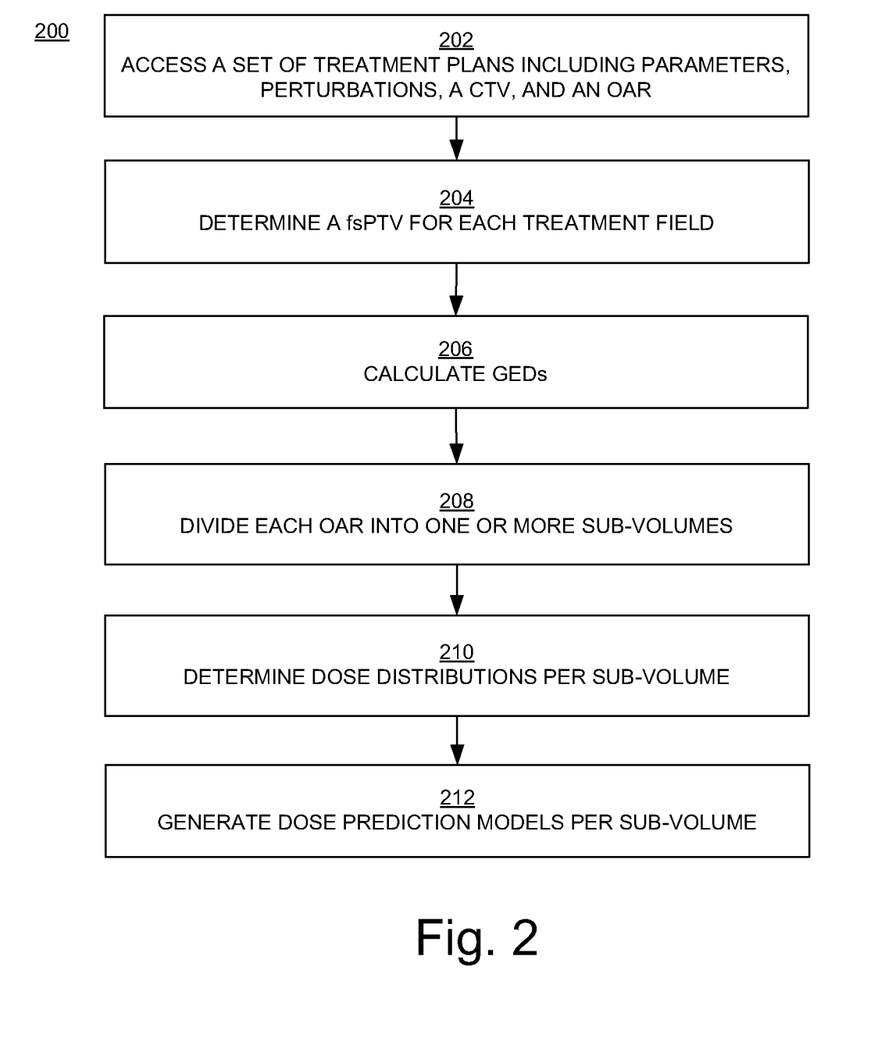
FIG. 2 is a flowchart of a computer-implemented method of generating a new and robust dose prediction model in embodiments according to the present invention.

FIG. 2 is a flowchart 200 of a computer-implemented method of generating a new and robust dose prediction model in embodiments according to the present invention. FIG. 2 is discussed with reference also to FIG. 3, which illustrates sub-volumes that are used when generating the dose prediction model.

In block 202 of FIG. 2, a set of previously defined treatment plans (which may be referred to herein as the training set) is selected and accessed from, for example, a database. The new dose prediction model is generated for a particular anatomical region (e.g., head and neck, or torso, etc.), and the training set will include treatment plans for the same anatomical region. In an embodiment, 20 or more treatment plans are accessed. In general, the number of plans that are accessed is sufficient to properly train and generate a robust dose prediction model. Thus, the number of plans that are selected can be more or less than 20, depending on the results of the training process. The number of plans that are selected may also depend on the anatomical region being modeled.

The selected treatment plans include nominal values of parameters that have an impact on the treatment dose to be delivered. The nominal values for a treatment plan may be stored in the plan itself or linked to the plan. In general, nominal values of the training set are accessed in block 202. These parameters may include, for example, patient movement (shifts of the isocenters of treatment fields with respect to patient position), beam calibration (e.g., changes in the computed tomography (CT) calibration curve), field size, beam attenuation, and imaging during planning and treatment.

Also in block 202, a number of perturbations (e.g., uncertainties, tolerances, ranges) of the nominal values are defined or accessed. Ideally, the perturbations are the same as those used to train the set of previously defined treatment plans, although the invention is not so limited. The perturbations for a treatment plan may be stored in the plan itself or linked to the plan.

Figure 3:
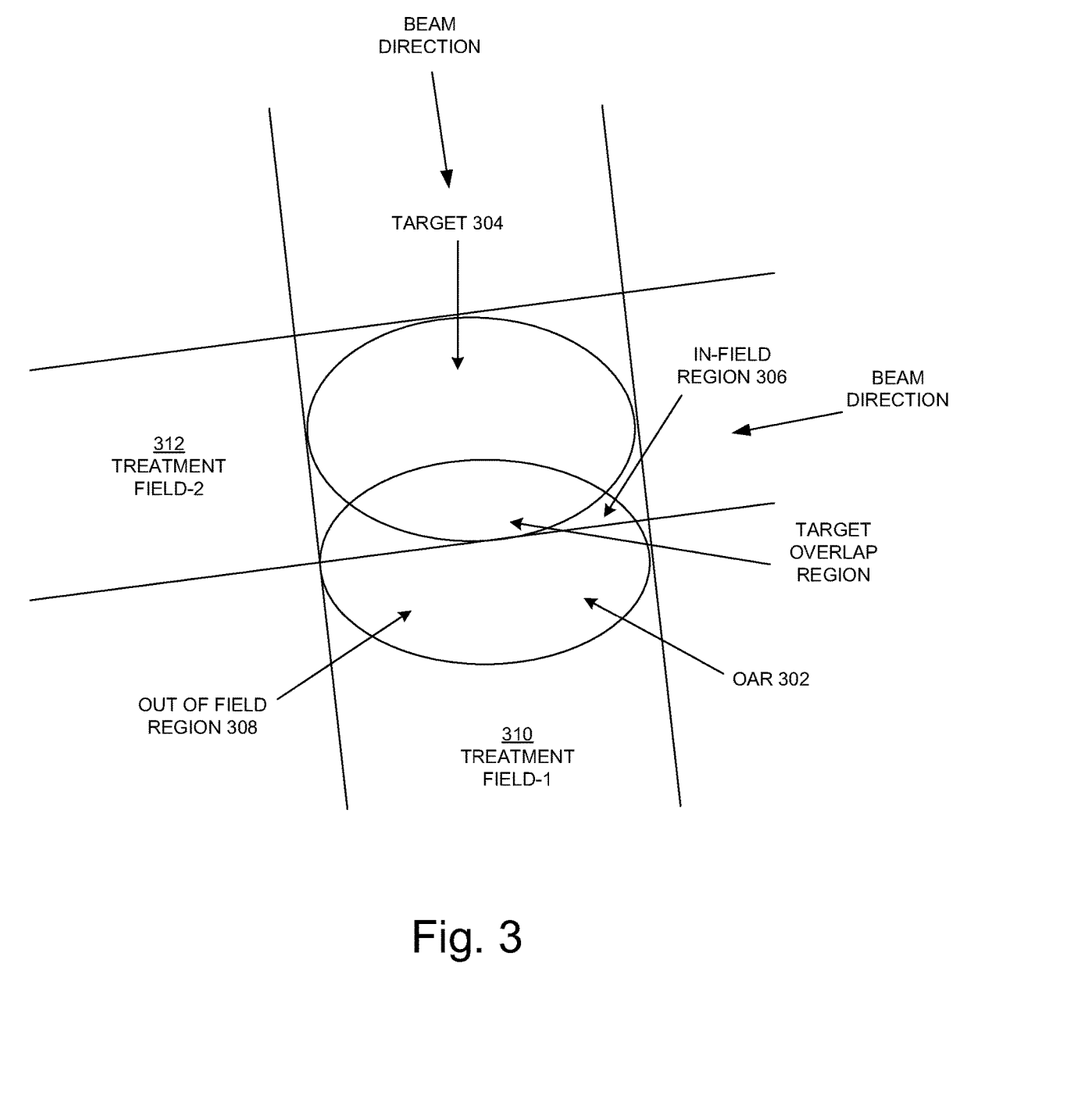
FIG. 3 illustrates sub-volumes that are used when generating a new and robust dose prediction model in embodiments according to the present invention.

Also in block 202, and with reference to FIG. 3, at least one OAR volume 302 is defined, and at least one clinical target volume (CTV) 304 is defined. The CTV 304 includes the target volume (e.g., the volume of the tumor being treated) and also accounts for uncertainties in the boundaries of the target volume (e.g., tumor spread that may not be imaged).

In block 204 of FIG. 2, a field-specific planning target volume (fsPTV) based on the perturbations is determined for each treatment field (e.g., the fields 310 and 312 of FIG. 3) of the predefined set of treatment plans. A planning target volume (PTV) includes the CTV and also accounts for the perturbations. A fsPTV is a separate PTV for each treatment field.

In block 206, in embodiments, a geometry-based expected dose (GED) is calculated using the fsPTV for each treatment field as the target volume. In essence, the GEDs provide an estimate of the dose distributions. The GEDs provide metrics that map the treatment beam and the patient's geometry to the DVHs.

In embodiments, a nominal GED is calculated using the nominal values of the parameters and using the fsPTV for each treatment field as the target volume. GEDs corresponding to the perturbations of the nominal values are then estimated using the nominal GED. More specifically, the nominal GED can be shifted laterally relative to a treatment beam according to an isocenter shift due to the perturbations (e.g., patient movement), or it can be shifted toward or away from the beam source due to, for example, perturbations associated with the CT image or calibration curve that affect the range of the beam.

In block 208, information that delineates the at least one CTV 304 and that delineates the at least one OAR volume 302 is accessed (from block 202), and each OAR volume is divided into one or more sub-volumes that are delineated based on spatial relationships between each OAR volume and the CTV and the fsPTV for each treatment field.

More specifically, in embodiments, the sub-volumes include: an in-field fsPTV region that includes at least a part of an OAR volume that overlaps with the projection of a fsPTV from at least one the treatment fields; an in-field CTV region that includes at least a part of an OAR volume that overlaps with the projection of a CTV from at least one of the treatment fields; an overlap fsPTV region that includes at least a part of an OAR volume that is inside a union of all of the fsPTVs; and an overlap CTV region that includes at least a part of an OAR volume that is inside any of the CTV(s). The term "projection" is a term of art and may be defined differently for different treatment modalities (e.g., beam types). For example, for a photon beam, it is the projection of the target treatment field in the beam direction, extending through the target volume. As another example, for a proton beam, it is the projection of the treatment field that is proximal to the target volume (between the beam source and the target volume, but not extending beyond the target volume).

In general, in embodiments, the in-field region 306 of FIG. 3 is divided into an in-field fsPTV region that includes at least a part of an OAR volume that overlaps with the projection of a fsPTV from at least one the treatment fields, and an in-field CTV region that includes at least a part of an OAR volume that overlaps with the projection of a CTV from at least one of the treatment fields; and the out-of-field region 308 of FIG. 3 is divided into an overlap fsPTV region that includes at least a part of an OAR volume that is inside a union of all of the fsPTVs, and an overlap CTV region that includes at least a part of an OAR volume that is inside any of the CTV(s).

In block 210 of FIG. 2, data is extracted from the treatment plans in the training set. More specifically, dose distributions are determined for each sub-volume identified in block 206. The dose distributions per sub-volume include a dose distribution based on the nominal values and dose distributions based on the perturbations. For example, if there are N perturbations, then N+1 dose distributions per sub-volume are determined per treatment plan: a dose distribution based on the nominal values, and a dose distribution based on each of the perturbations.

In block 212 (also during the data extraction phase), in the embodiments of FIG. 2, multiple dose prediction models are generated for each sub-volume. The models include a model trained using the dose distribution based on the nominal values and models trained using the dose distributions based on the perturbations. Thus, for example, if there are N perturbations, then N+1 dose prediction models are generated for each sub-volume, one model for each perturbation.

In an embodiment, each dose prediction model includes information that associates the model with the dose distribution used to train the model. Thus, for example, each dose prediction model has information that identifies the perturbation that it is associated with.

Figure 4:
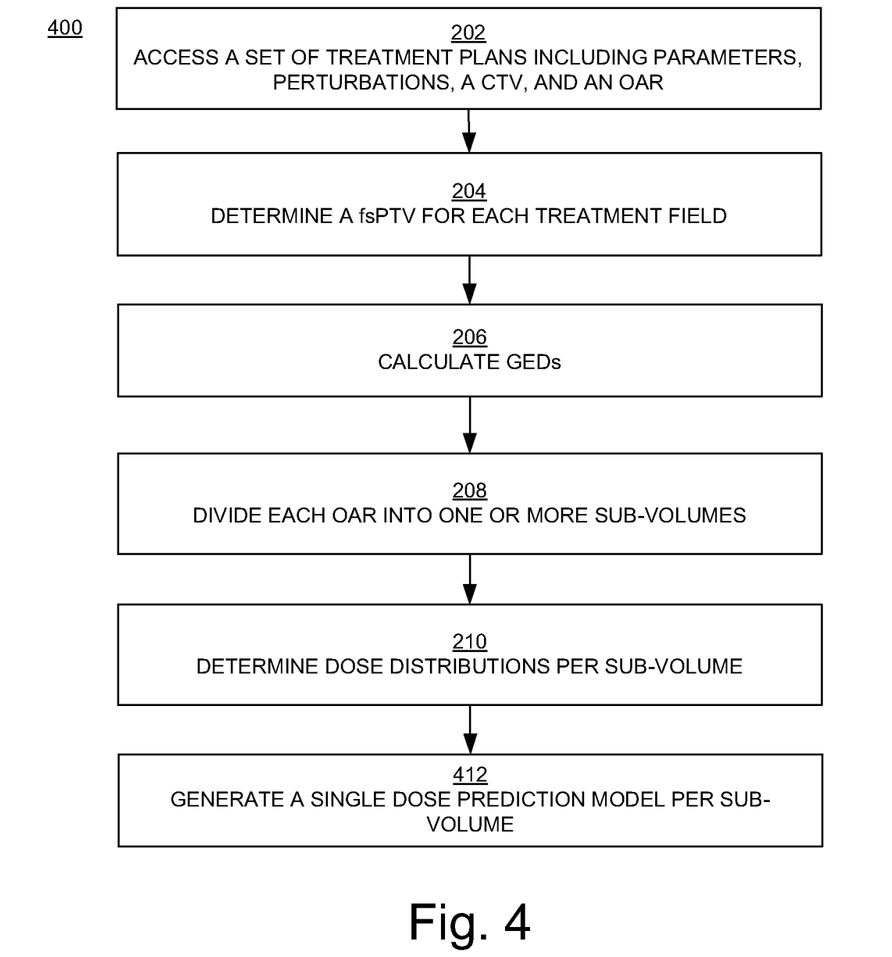
FIG. 4 is a flowchart of a computer-implemented method of generating a new and robust dose prediction model in other embodiments according to the present invention.

FIG. 4 is a flowchart 400 of a computer-implemented method of generating a new and robust dose prediction model in other embodiments according to the present invention. Blocks 202, 204, 206, 208, and 212 of FIG. 4 are described above in conjunction with FIG. 2. In the flowchart 400, block 412 replaces block 212 of FIG. 2.

In block 412 of FIG. 4 (during the data extraction phase), a single dose prediction model is generated for each sub-volume. However, that model is trained using all of the dose distributions. For example, if there are N perturbations plus the nominal values, then the dose prediction model is trained using N+1 dose distributions. In an embodiment, the dose prediction model includes information that associates the model with the dose distributions used to train the model.

Figure 5:
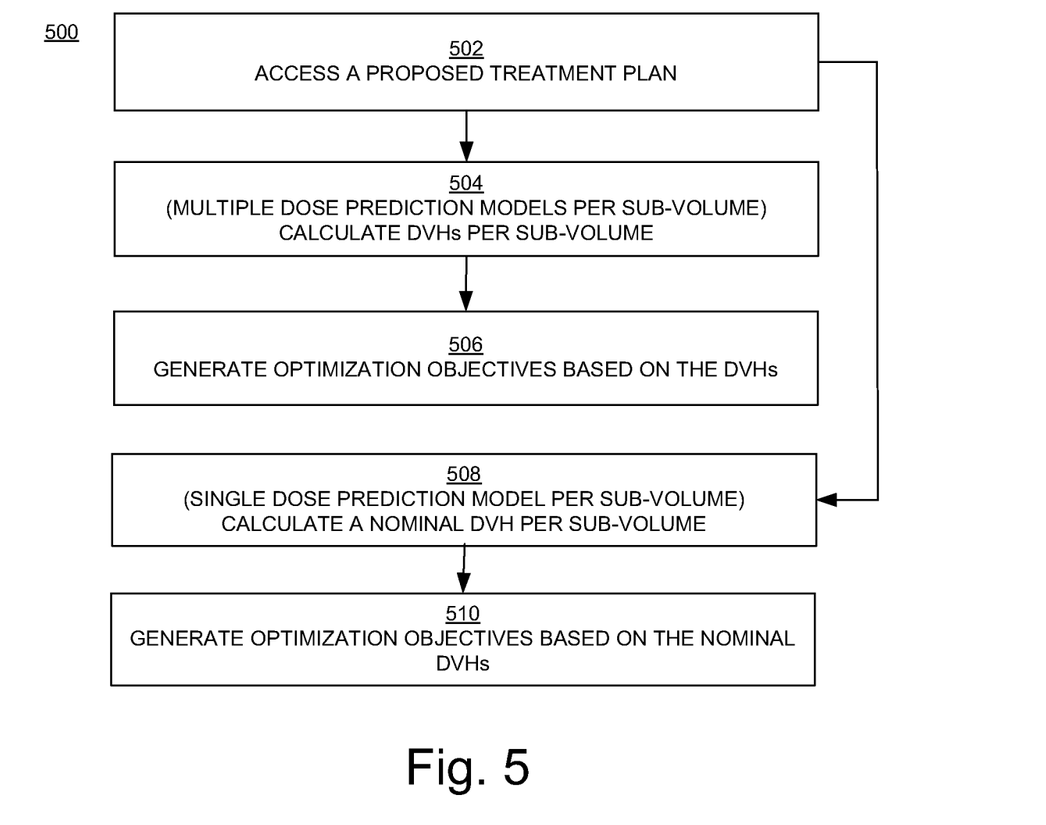
FIG. 5 is a flowchart of a computer-implemented method of applying a new and robust dose prediction model in embodiments according to the present invention.

FIG. 5 is a flowchart 500 of a computer-implemented method of applying a new and robust dose prediction model in embodiments according to the present invention.

In block 502, a proposed radiation treatment plan is accessed.

In block 504, in embodiments in which multiple robust dose prediction models are generated per sub-volume, DVHs are calculated for the radiation treatment plan. A DVH is calculated using the nominal values, and DVHs are calculated using the perturbations.

More specifically, in embodiments in which multiple robust dose prediction models are generated per sub-volume, when the models are applied to the proposed radiation treatment plan, the perturbations are inserted as parameters into the models to develop the optimization objectives. If there are N perturbations and therefore N+1 models, then a set of N+1 DVHs per sub-volume are determined for the plan.

In block 506, the dose prediction models are used to generate optimization objectives based on the DVHs. An optimization objective may be, for example, that the maximum dose in any of the perturbed scenarios for an OAR cannot exceed a certain value.

In block 508, in embodiments in which only a single robust dose prediction model per sub-volume is generated, that model is used to calculate a nominal DVH per-sub-volume.

In block 510, the dose prediction model is used to generate optimization objectives based on the nominal DVHs.

Figure 6:
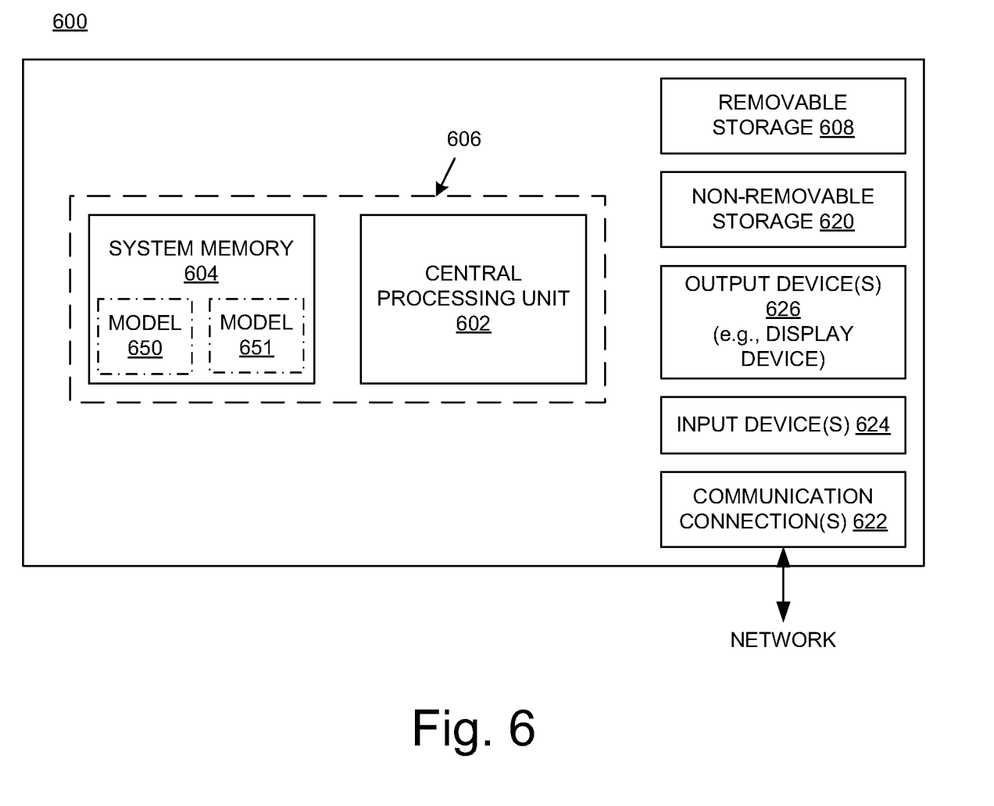
FIG. 6 is a block diagram of an example of a computer system upon which the embodiments described herein may be implemented.

FIG. 6 shows a block diagram of an example of a computer system 600 upon which the embodiments described herein may be implemented. In its most basic configuration, the system 600 includes at least one processing unit 602 and memory 604. This most basic configuration is illustrated in FIG. 6 by dashed line 606. The system 600 may also have additional features and/or functionality. For example, the system 600 may also include additional storage (removable and/or non-removable) including, but not limited to, magnetic or optical disks or tape. Such additional storage is illustrated in FIG. 6 by removable storage 608 and non-removable storage 620. The system 600 may also contain communications connection(s) 622 that allow the device to communicate with other devices, e.g., in a networked environment using logical connections to one or more remote computers.

The system 600 also includes input device(s) 624 such as keyboard, mouse, pen, voice input device, touch input device, etc. Output device(s) 626 such as a display device, speakers, printer, etc., are also included.

In the example of FIG. 6, the memory 604 includes computer-readable instructions, data structures, program modules, and the like associated with a model 650 for generating dose prediction models, and a model 651 for applying a dose prediction model to a radiation treatment plan, as described above in conjunction with FIGS. 1A, 2, 4, and 5. However, the models 650 and 651 may instead reside in any one of the computer storage media used by the system 600, or may be distributed over some combination of the computer storage media, or may be distributed over some combination of networked computers.

Thus, as described above, embodiments according to the present invention provide an improved method of radiation treatment planning. More specifically, embodiments according to the invention pertain to the generation of robust dose prediction models, and to the application of those models to develop and optimize radiation treatment plans. The robust dose prediction models are trained on and as such account for potential perturbations in plan parameters during treatment.

Embodiments according to the invention improve radiation treatment planning, and hence the treatment itself, by increasing the robustness of the dose prediction models, which are in turn used to develop and optimize radiation treatment plans for the benefit of the patients being treated. Robust models can be utilized to deliver sufficient doses to the CTV in perturbed treatment scenarios while ensuring that OARs do not receive too much dose in any perturbed scenario. Robust models are particularly important for proton beam treatments but are important as well for other modalities.

The dose prediction models are trained using a training set that includes multiple treatment plans, with multiple parameters that include nominal values and perturbations of the nominal values. For each of the plans, multiple fsPTV volumes are determined, and structures in the treatment region are divided into multiple sub-volumes. Dose distributions are determined considering all of these factors. Development of a dose prediction model or models is therefore a complex task that is beyond the capability of a human and relies on the use of a computing system.

Application of dose prediction models to proposed radiation treatment plans can also be a complex task. For example, depending on the treatment modality, the degrees of freedom available include beam shaping (collimation), beam weighting (spot scanning), beam intensity or energy, beam directions, dose rate, and number and arrangement of spots. Parameters such as those mentioned previously herein that can affect dose rate also are considered. If the target volume is divided into sub-volumes or voxels, then the values of the parameters can be on a per-sub-volume or per-voxel basis (e.g., a value per sub-volume or voxel). Therefore, consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method, comprising:
   accessing a plurality of treatment plans that have associated therewith perturbations of nominal values of parameters of the treatment plans;
   for each treatment field of the treatment plans, determining a field-specific planning target volume (fsPTV) based on the perturbations;
   accessing information that delineates at least one clinical target volume (CTV) and information that delineates at least one organ-at-risk (OAR) volume, wherein each said OAR volume comprises at least one sub-volume that is delineated based on spatial relationships between each said OAR volume and the CTV and the fsPTV for said each treatment field;
   determining dose distributions for each said sub-volume, wherein the dose distributions comprise a dose distribution based on the nominal values and dose distributions based on the perturbations; and
   generating dose prediction models for each said sub-volume, wherein the models comprise a model trained using the dose distribution based on the nominal values and models trained using the dose distributions based on the perturbations.

2. The method of claim 1, wherein each model of the dose prediction models comprises information that associates said each model with a dose distribution used to train said each model.

3. The method of claim 1, wherein the at least one sub-volume comprises a sub-volume selected from the group consisting of: an in-field fsPTV region comprising at least a part of an OAR volume that overlaps with a projection of a fsPTV from at least one of said each treatment field; an in-field CTV region comprising at least a part of an OAR volume that overlaps with a projection of a CTV from at least one of said each treatment field; an overlap fsPTV region comprising at least a part of an OAR volume that is inside a union of all fsPTVs; and an overlap CTV region comprising at least a part of an OAR volume that is inside any of said at least one CTV.

4. The method of claim 1, wherein said determining comprises calculating a geometry-based expected dose (GED).

5. The method of claim 4, wherein the GED is calculated using the fsPTV for said each treatment field as the target volume.

6. The method of claim 4, wherein said calculating comprises:
   calculating a nominal GED using the nominal values of the parameters and using the fsPTV for said each treatment field as the target volume; and
   using the nominal GED to estimate GEDs corresponding to the perturbations of the nominal values.

7. The method of claim 1, further comprising applying the dose prediction models to a radiation treatment plan.

8. The method of claim 7, wherein said applying comprises:
   calculating dose-volume histograms for the radiation treatment plan using the dose prediction models, wherein the dose-volume histograms comprise a dose-volume histogram calculated using the nominal values and dose-volume histograms calculated using the perturbations of the nominal values; and
   generating objectives of the radiation treatment plan using the dose prediction models and based on the dose-volume histograms.

9. A computer-implemented method, comprising:
   accessing a plurality of treatment plans that have associated therewith perturbations of nominal values of parameters of the treatment plans;
   for each treatment field of the treatment plans, determining a field-specific planning target volume (fsPTV) based on the perturbations;
   accessing information that delineates at least one clinical target volume (CTV) and information that delineates at least one organ-at-risk (OAR) volume, wherein each said OAR volume comprises at least one sub-volume that is delineated based on spatial relationships between each said OAR volume and the CTV and the fsPTV for said each treatment field;
   determining a plurality of dose distributions comprising a dose distribution based on the nominal values and dose distributions based on the perturbations; and
   generating a dose prediction model for each said sub-volume, the model trained using the plurality of dose distributions.

10. The method of claim 9, wherein the dose prediction model comprises information that associates the dose prediction model with the dose distributions used to train the dose prediction model.

11. The method of claim 9, wherein the at least one sub-volume comprises a sub-volume selected from the group consisting of: an in-field fsPTV region comprising at least a part of an OAR volume that overlaps with a projection of a fsPTV from at least one of said each treatment field; an in-field CTV region comprising at least a part of an OAR volume that overlaps with a projection of a CTV from at least one of said each treatment field; an overlap fsPTV region comprising at least a part of an OAR volume that is inside a union of all fsPTVs; and an overlap CTV region comprising at least a part of an OAR volume that is inside any of said at least one CTV.

12. The method of claim 9, wherein said determining comprises calculating a geometry-based expected dose (GED).

13. The method of claim 12, wherein the GED is calculated using the fsPTV for said each treatment field as the target volume.

14. The method of claim 12, wherein said calculating comprises:

calculating a nominal GED using the nominal values of the parameters and using the fsPTV for said each treatment field as the target volume; and using the nominal GED to estimate GEDs corresponding to the perturbations of the nominal values.

15. The method of claim 9, further comprising applying the dose prediction model to a radiation treatment plan.

16. The method of claim 15, wherein said applying comprises:

calculating dose-volume histograms for the radiation treatment plan using the dose prediction model and using the nominal values; and generating objectives of the radiation treatment plan using the dose prediction model and based on the dose-volume histograms.

17. A computer-implemented method, comprising:

accessing a radiation treatment plan;

calculating dose-volume histograms for the radiation treatment plan using a plurality of dose prediction models, wherein the dose prediction models have associated therewith nominal values of parameters of the radiation treatment plan and perturbations of the nominal values, and wherein said calculating comprises:

calculating a dose-volume histogram using the nominal values; and calculating dose-volume histograms using the perturbations; and generating objectives of the radiation treatment plan using the plurality of dose prediction models and based on the plurality of dose-volume histograms for the radiation treatment plan.

18. The method of claim 17, wherein said calculating a dose-volume histogram using the nominal values comprises using a dose prediction model trained using the nominal values.

19. The method of claim 18, wherein said calculating dose-volume histograms using the perturbations comprises using dose prediction models trained using the perturbations.

20. The method of claim 17, wherein each model of the plurality of dose prediction models comprises information that associates said each model with a dose distribution used to train said each model.

\* \* \* \* \*